United States Patent
Toyama et al.

(10) Patent No.: US 8,563,771 B2
(45) Date of Patent: Oct. 22, 2013

(54) PROCESS FOR PRODUCTION OF PRECURSOR COMPOUND FOR RADIOACTIVE HALOGEN-LABELED ORGANIC COMPOUND

(75) Inventors: Masahito Toyama, Sodegaura (JP); Akio Hayashi, Sodegaura (JP)

(73) Assignee: Nihon Medi-Physics Co., Ltd., Tokyo (JP)

(*) Notice: Subject to any disclaimer, the term of this patent is extended or adjusted under 35 U.S.C. 154(b) by 672 days.

(21) Appl. No.: 12/448,311

(22) PCT Filed: Dec. 17, 2007

(86) PCT No.: PCT/JP2007/074220
§ 371 (c)(1), (2), (4) Date: Jun. 17, 2009

(87) PCT Pub. No.: WO2008/078589
PCT Pub. Date: Jul. 3, 2008

(65) Prior Publication Data
US 2010/0016626 A1   Jan. 21, 2010

(30) Foreign Application Priority Data
Dec. 27, 2006   (JP) .................... 2006-351883

(51) Int. Cl.
*C07C 61/04*   (2006.01)
(52) U.S. Cl.
USPC .......................................... 562/505
(58) Field of Classification Search
None
See application file for complete search history.

(56) References Cited

U.S. PATENT DOCUMENTS

| | | | |
|---|---|---|---|
| 5,808,146 A * | 9/1998 | Goodman et al. | ............ 562/504 |
| 5,817,776 A | 10/1998 | Goodman et al. | |
| 7,264,792 B2 | 9/2007 | Gibson et al. | |
| 2004/0236085 A1 | 11/2004 | Luthra et al. | |
| 2006/0039855 A1 | 2/2006 | Gibson et al. | |

(Continued)

FOREIGN PATENT DOCUMENTS

| | | |
|---|---|---|
| EP | 2 017 258 A1 | 1/2009 |
| JP | 2000-500442 A | 1/2000 |

(Continued)

OTHER PUBLICATIONS

PCT International Preliminary Report on Patentability in PCT/JP2007/074220 dated Jun. 30, 2009.

(Continued)

*Primary Examiner* — Karl J Puttlitz
(74) *Attorney, Agent, or Firm* — Fitch, Even, Tabin & Flannery, LLP (57) ABSTRACT

A process is provided for producing a labeled precursor which is useful for production of a radioactive fluorine-labeled amino acid compound. In the reaction step for introducing a leaving group to a mixture of syn-form and anti-form of FACBC, a base is allowed to present in the reaction system to produce a syn-leaving group adduct, which is unreactive with the base and is highly stable, and an anti-leaving group adduct which can react with the base to form a water-soluble compound. By employing a purification method utilizing such a difference in solubility, the syn-leaving group adduct can be separated selectively. The base may be a linear- or branched-chain primary to tertiary alkylamine having 1 to 10 carbon atoms, a nitrogen-containing heterocyclic compound with 2 to 20 carbon atoms, and a nitrogen-containing hetero aromatic compound with 2 to 20 carbon atoms.

9 Claims, 1 Drawing Sheet 1) sat. Ba(OH)₂ aq., reflux, 24h or more; 2) SOCl₂, Et₃N, EtOH, −78°C~reflux, 21h; 3) EtOH : Et₃N = 9:1, rt., Boc₂O, 18h (3 steps 56%); 4) palladium-activated carbon, EtOH, rt., 21h (44%); 5) pyridine, trifluoromethanesulfonyl anhydride, 0°C, 30min (58%).

(56) References Cited

U.S. PATENT DOCUMENTS

| | | | |
|---|---|---|---|
| 2006/0292073 A1 | 12/2006 | Goodman et al. |
| 2008/0281121 A1 | 11/2008 | Ito et al. |
| 2009/0105489 A1 | 4/2009 | Toyama et al. |

FOREIGN PATENT DOCUMENTS

| | | | |
|---|---|---|---|
| JP | 2006-510706 A | | 3/2006 |
| RU | 2003137589 A | | 5/2005 |
| WO | WO97/17092 | | 5/1997 |
| WO | 2004056725 | * | 7/2004 |
| WO | WO2004/056725 | | 7/2004 |
| WO | WO 2004/056725 A1 | | 7/2004 |
| WO | WO2006/037950 | | 4/2006 |
| WO | WO2006/126410 | | 11/2006 |
| WO | WO2007/001958 | | 1/2007 |
| WO | WO2007/063824 | | 6/2007 |
| WO | WO2007/132689 | | 11/2007 |

OTHER PUBLICATIONS

PCT Written Opinion of the International Searching Authority in PCT/JP2007/074220.
Wang et al., Heteratom Chemistry, vol. 13, No. 1, pp. 77-83 (2002).
Shoup et al., J. Labelled Cpd. and Radiopharm. 42:215-225 (1999).
Communication with Supplementary European Search Report, Dec. 2, 2011 in EPO application 07 85 0708,4.
Supplementary European Search Report, dated Oct. 26, 2010 in EPO Application 08863261.7.
Office Action dated Oct. 1, 2010, in Russian Application 2008126277/04(032044) (Russian translation).
Communication from European Patent Office in EP Application 06833463.0, dated Jul. 14, 2010.
Examination Report issued on Feb. 17, 2010, in New Zealand Application No. 568179.
Lijuan J. Wang et al., "Syntheses of New Conformationally Constrained S-[2-[(1-Iminoethyl) amino]ethyl]homocysteine Derivatives as Potential Nitric Oxide Synthase Inhibitors", Heteroatom Chemistry, vol. 13, No. 1, pp. 77-83 (2002).
Laurent Martarello et al., "Synthesis of *syn*- and *anti*-1-Amino-3-[18F]fluoromethyl-cyclobutane-1-carboxylic Acid (FMACBC), Potential PET Ligands for Tumor Detection", *Journal of Medicinal Chemistry*, vol. 45, No. 11, pp. 2250-2259 (2002).
Timothy M. Shoup et al., "Synthesis of [$^{18}$F]1-Amino-3-fluorocyclobutane-l-carboxylic Acid (FACBC): A Pet Tracer for Tumor Delineation", *The Journal of Labelled Compounds and Radiopharmaceuticals*, 42(3):215-225 (1999).
Timothy M. Shoup et al., "Synthesis and Evaluation of [$^{18}$F]1-Amino-3-fluorocyclobutane-1-carboxylic Acid to Image Brain Tumors", *The Journal of Nuclear Medicine*, vol. 40, No. 2, pp. 331-338 (1999).
Russian Office Action corresponding with Russian Patent Application No. 2009128664/04(039866).
Chinese Office Action dated Dec. 16, 2011, corresponding with CN Patent Application No. 200780048213.X.
Jonathan McConathy et al. "Improved synthesis of anti-[18F]FACBC: improved preparation of labeling precursor and automated radiosynthesis", Applied Radiation and Isotope, vol. 58, 2003, pp. 657-666.
Russian Offical Decsion of Grant issued in Russian Application 2009128664/04.
JPO Office Action apparently issued on Jan. 22, 2013 in JP Appln. 2008-551038.
Chinese Office Action dated Dec. 7, 2012, corresponding with CN Patent Application No. 200780048213.X, with English-language translation, entire document, 12 pages.
Communication from EPO dated Sep. 4, 2012 that issued in EPO appln. 07850708.4.
Chinese Office Action dated Jun. 28, 2013, corresponding with CN Patent Application No. 200780048213.X, with English-language translation, entire document, 14 pages.

* cited by examiner 1) sat. Ba(OH)₂ aq., reflux, 24h or more; 2) SOCl₂, Et₃N, EtOH, −78℃~reflux, 21h; 3) EtOH: Et₃N = 9:1, rt., Boc₂O, 18h (3steps 56%); 4) palladium-activated carbon, EtOH, rt., 21h (44%); 5) pyridine, trifluoromethanesulfonyl anhydride, 0℃, 30min (58%).

PROCESS FOR PRODUCTION OF PRECURSOR COMPOUND FOR RADIOACTIVE HALOGEN-LABELED ORGANIC COMPOUND

CROSS-REFERENCE TO RELATED APPLICATIONS

This is a U.S. National Phase of International Application PCT/JP2007/074220, filed Dec. 17, 2007, and claims the benefit of foreign priority under 35 U.S.C. §119 based on JP 2006-351883, filed Dec. 27, 2006, the entire disclosures of which are hereby incorporated herein by reference.

TECHNICAL FIELD

The present invention relates to a process for producing an organic compound which can suitably be used for production of a radioactive halogen-labeled organic compound that is an effective ingredient of agents used for positron emission tomography (PET).

BACKGROUND

Nuclear medicine examination enables diagnosis by administrating an agent containing a compound labeled with a specific radioisotope as an effective ingredient (hereinafter referred to as "radiopharmaceutical") intravenously to a human body and detecting a radiation emitted from the compound, followed by imaging information obtained from the radiation thereof. Nuclear medicine examination is effective in diagnosing a variety of diseases including heart disease and cancer, and characteristic in that it has not only high specificity and sensitivity to diseases, but also an advantage of providing information on the functionality of lesions, compared to other examination techniques.

In addition, radiopharmaceuticals are produced by labeling an unlabeled compound (hereinafter referred to as "labeling precursor") when necessary, and conducting preparation operations such as purification. Therefore, the labeling precursor is very important as a raw material for synthesizing an effective ingredient, and a method for producing a low-cost and large amount of labeling precursor is requisite for development of radiopharmaceuticals.

Recently, [$^{18}$F]1-amino-3-fluorocyclobuthanecarboxylic acid (hereinafter referred to as [$^{18}$F]-FACBC) is researched and developed as a novel radiopharmaceutical. [$^{18}$F]-FACBC is expected to be developed as a tumor diagnostic agent since it is considered to have a property of being taken up into a cell via an amino acid transporter and largely taken up into tumor cells which are highly proliferative and active in protein synthesis.

It is known that as [$^{18}$F]-FACBC, there exist compounds different in stereoisomer, which are called syn-form and anti-form (hereinafter referred to as syn-[$^{18}$F]-FACBC or anti-[$^{18}$F]-FACBC). Since stereoisomers are usually different in physical and chemical properties, syn-[$^{18}$F]-FACBC and anti-[$^{18}$F]-FACBC are defined as different compounds in the development of pharmaceuticals. Therefore, when [$^{18}$F]-FACBC is used as an effective ingredient of a pharmaceutical, the pharmaceutical must have a composition comprising substantially either one of the stereoisomers.

On the other hand, the method for producing a low-cost and large amount of a labeling compound is important for [$^{18}$F]-FACBC. Generally, as labeling precursors of radioactive compounds labeled with $^{18}$F, compounds in which a leaving group such as triflate is introduced at sites to be labeled are used, and such compounds are usually produced as follows. First, a compound which is substituted by OH group at a position of $^{18}$F of a radioactive compound is synthesized. Then, a leaving group such as triflate is introduced to the OH group, and a protecting group is further introduced if necessary. The same synthesis method is disclosed for the labeling precursor of [$^{18}$F]-FACBC (Patent Document 1).

By the way, for a [$^{18}$F]-FACBC, inversion occurs in the step of introducing $^{18}$F. Therefore, for example, in the synthesis of the labeling precursor used for the synthesis of anti-[$^{18}$F]-FACBC, a compound in which the OH group is introduced at the syn-position opposite to the $^{18}$F position must be synthesized. Similarly, in the synthesis of the labeling precursor used for the synthesis of syn-[$^{18}$F]-FACBC, a compound in which the OH group is introduced at the anti-position must be synthesized.

For convenience, compounds are hereinafter abbreviated and represented as follows. As required, the term anti- or syn-which indicates a stereoisomer is prefixed, and the case where it is not prefixed means a mixture thereof.

Protected form: an FACBC in which an amino group and a carboxyl group thereof are protected.
OH form: a protected form to which an OH group is introduced at a position to which $^{18}$F is to be introduced.
Leaving group adduct: an OH form to which a leaving group is introduced at an OH group thereof.

International Publication No. WO97/017092 pamphlet discloses a method for synthesizing 1-t-butylcarbamate-3-trifluoromethanesulfonoxy-cyclobutane-1-carboxylic acid methyl ester as a labeling precursor of [$^{18}$F]-FACBC (Patent Document 1).

International Publication No. WO04/056725 pamphlet discloses a method for synthesizing syn-1-t-butoxycarbonylamino-3-[1,2,3,4-tetrafluoro-2-(1,1,2,2-tetrafluoro-2-iodoethoxy)ethanesulfonyloxy]-cyclobutane carboxylic acid methyl ester as a labeling precursor of anti-[$^{18}$F]-FACBC. This is, as mentioned above, a method of synthesizing a syn-OH form, and then synthesizing a syn-leaving group adduct.

Patent Document 1: International Publication No. WO97/017092 pamphlet
Patent Document 2: International Publication No. WO04/056725 pamphlet

DISCLOSURE OF THE INVENTION

Problem to be Solved by the Invention

As mentioned above, International Publication No. WO97/017092 pamphlet discloses a method for synthesizing a labeling precursor of [$^{18}$F]-FACBC. However, the publication does not differentiate any stereoisomer at each step.

International Publication No. WO04/056725 pamphlet discloses a method for synthesizing syn-1-t-butoxycarbonylamino-3-[1,2,3,4-tetrafluoro-2-(1,1,2,2-tetrafluoro-2-iodoethoxy)ethanesulfonyloxy]-cyclobut anecarboxylic acid methyl ester as a labeling precursor of anti-[$^{18}$F]-FACBC. However, this is complicated in that each step until the synthesis of an anti-OH form requires purification of a stereoisomer.

The present invention has been made in view of the above circumstances, and aimed at providing a simple method for producing a syn-leaving group adduct as a precursor of anti-[$^{18}$F]-FACBC.

Means for Solving the Problem

As a result of diligent researches, the present inventors have found that the syn-leaving group adduct and the anti-leaving group adduct have a difference in reactivity with a base. When a specific base is added to a reaction system at a step of introducing a leaving group, the syn-leaving group adduct which is water-insoluble shows no reactivity with the base and is stable. On the other hand, the anti-leaving group adduct easily reacts with the base, and becomes a water-soluble compound. By selecting a purification method utilizing the difference in solubility between the leaving group adducts, the syn-leaving group adduct can selectively be obtained without any complicated purification even from a mixture of the syn-OH form and the anti-OH form by adding thereto a specific base to effect the reaction at the step of introducing a leaving group.

The present process for producing a precursor compound of an anti-[$^{18}$F]-FACBC is characterized in that it comprises;

a reaction step of giving a reaction condition to a solution containing a compound represented by the following formula (1):

together with a compound which reacts with the OH group of the compound represented by the formula (1) to become a leaving group, and a base, and a purification step of purifying a reaction solution resulting from the reaction step to obtain a substantially single stereoisomer of a compound represented by the following formula (2):

$R_1$ represents a protective group of a carboxyl group, and is not particularly limited as long as it is a protecting group used for carboxyl group. Preferably, a straight-chain or branched-chain alkyl group with 1-5 carbon atoms, or an aromatic substituent can be used. More preferably, methyl group, ethyl group, t-butyl group or phenyl group can be used.

$R_2$ represents a protective group of an amino group, and is not particularly limited as long as it is a protecting group used for an amino group. Preferably, a straight-chain or branched-chain alkyloxycarbonyl substituent with 2-7 carbon atoms, a straight-chain or branched-chain alkenyloxycarbonyl substituent with 3-7 carbon atoms, a saturated or unsaturated alkylcarbonyl group with 2-7 carbon atoms, a benzyloxycarbonyl substituent with 7-12 carbon atoms, an alkyldithiooxycarbonyl substituent with 2-7 carbon atoms, a straight-chain or branched-chain alkylamide substituent with 1-6 carbon atoms, a straight-chain or branched-chain alkenylamide substituent with 2-6 carbon atoms, a benzamide substituent with 6-11 carbon atoms, an aromatic imine substituent with 6-11 carbon atoms, a straight-chain or branched-chain alkylamine substituent with 1-6 carbon atoms, a straight-chain or branched-chain alkenylamine substituent with 2-6 carbon atoms or a benzylamine substituent with 6-11 carbon atoms can be used. More preferably, t-butoxycarbonyl group, aryloxycarbonyl group or N-benzylideneamine substituent can be used.

Examples of the compound which reacts with the OH group of the compound represented by the formula (1) to become a leaving group in the reaction step include a straight-chain or branched-chain alkylsulfonic acid with 1-10 carbon atoms, a straight-chain or branched-chain haloalkylsulfonic acid with 1-9 carbon atoms, an aromatic sulfonic acid and an aromatic sulfonic acid chloride. As a straight-chain or branched-chain alkylsulfonic acid with 1-10 carbon atoms, methanesulfonic acid is preferably used. As a straight-chain or branched-chain haloalkylsulfonic acid with 1-9 carbon atoms, trifluoromethanesulfonic acid is preferably used. As the aromatic sulfonic acid, a compound selected from the group consisting of toluenesulfonic acid, nitrobenzenesulfonic acid and benzenesulfonic acid is preferably used. As the aromatic sulfonic acid chloride, a compound selected from the group consisting of toluenesulfonic acid chloride, benzenesulfonic acid chloride and nitrobenzenesulfonic acid chloride is preferably used.

Examples of the base added in the reaction step are one or more selected from the group consisting of a straight-chain or branched-chain primary to tertiary alkylamine with 1-10 carbon atoms, nitrogen-containing heterocyclic compound with 2-20 carbon atoms and nitrogen-containing hetero aromatic compound with 2-20 carbon atoms. As the primary to tertiary alkylamine, ethylamine, propylamine, isopropylamine, dimethylamine, diethylamine, dipropylamine, diisopropylamine, trimethylamine, triethylamine or tripropylamine is preferably selected. As the nitrogen-containing heterocyclic compound, pyrrolidine, imidazoline, pyrazolidine, piperidine, piperazine, 1,4-diazabicyclo[2.2.2.]octane, pyrroline, aziridine or 1,8-diazabicyclo[5.4.0]undeca-7-ene is preferably selected. As the nitrogen-containing hetero aromatic compound, pyrrole, pyridine, pyrimidine, pyrazine, triazine, imidazole or pyrazole is preferably selected. More preferably, pyridine is preferably used.

The solvent used in the reaction step is not particularly limited as long as it is a solvent which can dissolve the compound represented by the formula (1) as well as the compound reacting with the OH group of that compound to become a leaving group and a base, and has no reactivity with these compounds. Preferably, a polar solvent can be used, and more preferably chloroform and pyridine are used.

The reaction temperature in the reaction step is preferably a temperature lower than room temperature, more preferably not more than 4° C. and most preferably around 0° C. In this instance, it should be noted that if the reaction temperature is too high, it will often become a cause of generation of a by-product. The reaction temperature only has to be a temperature not less than the solidifying point of the solvent. However, it should be noted that if the reaction temperature is too low, the reaction progress will often become too slow. A preferable embodiment includes a method of performing the reaction at a controlled temperature under ice bath or cooled solvent. The reaction time is not particularly limited as long as it is a time sufficient for the reaction to proceed.

As a purification process in the purification step, various processes utilizing a difference in solubility can be used. Preferably, a purification process such as a liquid-liquid extraction process, a column separation process and a slurry purification process can be used. More preferably, a liquid-liquid extraction process can be used.

Effect of the Invention

According to the present invention, it has been made possible to easily and efficiently obtain a syn-leaving group adduct which is a labeling precursor useful for obtaining anti-[$^{18}$F]-FACBC.

BEST MODE FOR CARRYING OUT THE INVENTION

Next, a process for producing a compound of the present invention will be described taking, as an example, a production of syn-1-(N-(t-butoxycarbonyl)amino)-3-[((trifluoromethyl)sulfonyl)oxy]-cyclobutane-1-carboxylic acid ethyl ester.

First, a solution of 5-(3-benzyloxycyclobutane)hydantoin in a saturated barium hydroxide solution is refluxed, and sulfuric acid is added to the refluxed solution to adjust the pH of the same to about 7. The solution is then filtered and the filtrate is concentrated to allow 1-amino-3-benzyloxycyclobutane-1-carboxylic acid to precipitate as white crystals (Step 1). The acid used for the pH adjustment may be an acid other than sulfuric acid, but it needs to be an acid that forms a water-insoluble inorganic salt with barium. Meanwhile, in the present invention, a stereoisomer of 5-(3-benzyloxycyclobutane)hydantoin used in this step does not require purification, and a mixture of syn-form/anti-form can be used as it is.

Next, the resulting 1-amino-3-benzyloxycyclobutane-1-carboxylic acid is fully dried to remove water and then dissolved in ethanol. A base and thionyl chloride are then added to the ethanol solution in this order, stirred at room temperature, and then heated under reflux at about 95° C. After the reaction has fully progressed, the solution is concentrated under reduced pressure to yield 1-amino-3-benzyloxycyclobutane-1-carboxylic acid ethyl ester as white crystals (Step 2).

The base added to the reaction solution in the above step may be any base that can trap the hydrochloric acid produced during the reaction. Preferably triethylamine can be used. The amount of the base to be used is the same as or larger than that of thionyl chloride.

The amount of thionyl chloride needs to be the same as or larger than that of the reaction raw material, namely, 1-amino-3-benzyloxycyclobutane-1-carboxylic acid. If the amount of thionyl chloride is too small, it unfavorably occurs that ethyl esterification fails to progress sufficiently. If the amount of thionyl chloride is too large, excess hydrochloric acid is produced, and thus a larger amount of base is unfavorably required. In preferred embodiments, the amount of thionyl chloride is equal to or smaller than 5 equivalents of 1-amino-3-benzyloxycyclobutane-1-carboxylic acid.

Figure 1:
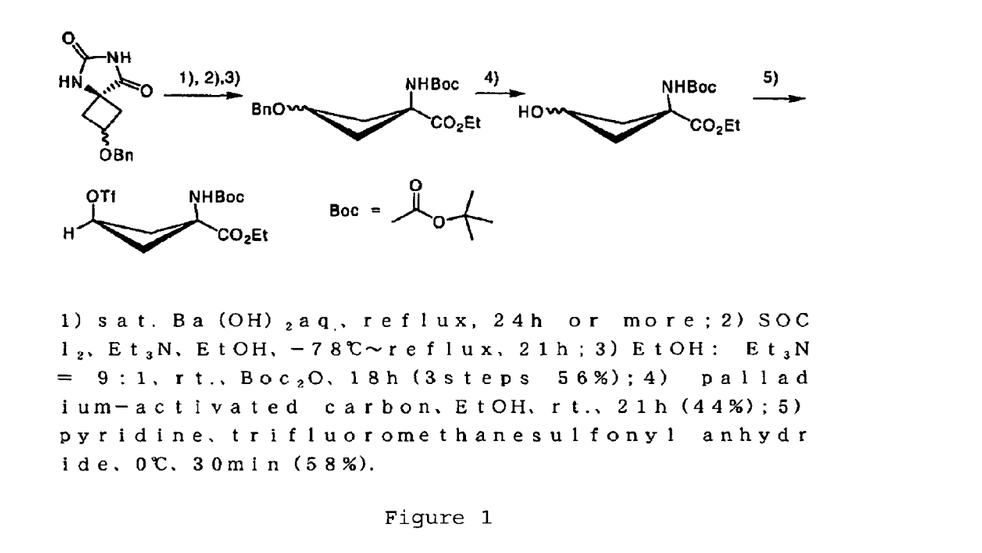
FIG. 1 shows a scheme of synthesis of syn-1-(N-(t-butoxycarbonyl)amino)-3-[((trifluoromethyl)sulfonyl)oxy]-cyclobutane-1-carboxylic acid ethyl ester when syn/anti-hydantoin is used as a starting material.

Then, 1-amino-3-benzyloxycyclobutane-1-carboxylic acid ethyl ester is added to a solution of a small amount of base in an alcohol solvent such as ethanol. The resultant suspension is stirred under cooling, and t-butyl dicarbonate is added to the suspension to allow them to react at room temperature (FIG. 1, Step 3). As the alcohol solvent, ethanol can be preferably used, though various kinds of alcohol can be used. The amount of the base is required to be sufficiently small relative to that of the alcohol, but if the amount is too small, the progress of the reaction becomes slow unfavorably. In preferred embodiments, a solution in which the ratio of alcohol to base is 9:1 is used. The amount of t-butyl dicarbonate needs to be one equivalent or more of 1-amino-3-benzyloxycyclobutane-1-carboxylic acid, and is preferably 1.5 equivalents of 1-amino-3-benzyloxycyclobutane-1-carboxylic acid.

This operation makes it possible to yield 1-(N-(t-butoxycarbonyl)amino)-3-benzyloxy-cyclobutane-1-carboxylic acid ethyl ester.

The 1-(N-(t-butoxycarbonyl)amino)-3-benzyloxy-cyclobutane-1-carboxylic acid ethyl ester synthesized as above is dissolved in an alcohol solvent such as ethanol or an acetate ester solvent such as ethyl acetate ester, and palladium-on-activated carbon (amount: 10 w/w % or more relative to the substrate) is added to the solution in an atmosphere of hydrogen to allow them to react under stirring at room temperature. The reaction solution is then filtered through Celite, and the filtrate is concentrated and purified to yield 1-(N-(t-butoxycarbonyl)amino)-3-hydroxy-cyclobutane-1-carboxylic acid ethyl ester (Step 4).

The resultant 1-(N-(t-butoxycarbonyl)amino)-3-hydroxy-cyclobutane-1-carboxylic acid ethyl ester is dissolved in an organic solvent such as diethylether. Then, syn-1-(N-(t-butoxycarbonyl)amino)-3-[((trifluoromethyl)sulfonyl)oxy]-cyclobutane-1-carboxylic acid ethyl ester is yielded by adding a base and trifluoromethanesulfonic anhydride to the resultant solution and giving thereto a reaction condition (Step 5). In the present invention, a stereoisomer of 1-(N-(t-butoxycarbonyl)amino)-3-hydroxy-cyclobutane-1-carboxylic acid ethyl ester used in this step does not require purification, and a mixture of syn-form/anti-form can be used as it is, unlike the methods disclosed before (for example, the method described in the reference (International Publication No. WO04/056725 pamphlet)).

As the base, an alkylamine, a nitrogen-containing heterocyclic compound and a nitrogen-containing hetero aromatic compound can be used. In a preferable embodiment, pyridine is used as a solvent for dissolving as well as a base.

Finally, by purifying the reaction solution, the target compound syn-1-(N-(t-butoxycarbonyl)amino)-3-[((trifluoromethyl)sulfonyl)oxy]-cyclobutane-1-carboxylic acid ethyl ester can be obtained as a substantially single stereoisomer. As a preferable purification process, a liquid-liquid extraction process can be used in which water, an organic solvent such as ether and an acid are added to the reaction solution to purify the organic layer.

Compounds of the present invention other than the above described one can also be synthesized through the steps similar to those described above. For example, when a compound is synthesized in which a haloalkylsulfonic acid ester substituent other than the triflate substituent, an alkylsulfonic acid ester substituent or an aromatic sulfonic acid ester substituent is bound to the carbon atom at position 3 of the cyclobutane ring, the reaction in the step 5 can be carried out in the same manner as above, except that a different halogen sulfonyl or sulfonic anhydride is used instead of trifluoromethanesulfonic anhydride.

When a compound is synthesized in which an alkyloxycarbonyl substituent other than the t-butoxycarbonyl substituent, an alkenyloxycarbonyl substituent or a benzyloxycarbonyl substituent is bound to the amino group at position 1, the reaction in the above described step 3 can be performed using various alkylchloroformates, alkenylchloroformates or benzylchloroformates respectively, instead of t-butyl dicarbonate. Similarly, a compound in which an aromatic imine substituent is bound to the amino group can be synthesized by allowing benzaldehyde having a substituent to react with the amino group in the step 3.

When a 1-propylester form and an isopropylester form are synthesized, 1-propanol and isopropanol may be used, respectively, as the alcohol for the reaction in the above step 2.

Next, as an example of use of the novel amino acid organic compounds according to the present invention, a method will be described in which anti-[$^{18}$F]FACBC is synthesized using the above synthesized syn-1-(N-(t-butoxycarbonyl)amino)-3-[((trifluoromethyl)sulfonyl)oxy]-cyclobutane-1-carboxylic acid ethyl ester.

The synthesis of anti-[$^{18}$F]FACBC is carried out in two steps: a step of adding radioactive fluorine to the precursor; and a step of deprotecting the compound to which radioactive fluoride has been added.

Radioactive fluorine can be obtained by a known method, for example, a method in which $H_2{}^{18}O$ enriched water is used as a target and exposed to proton bombardment. In this instance, radioactive fluorine exists in the $H_2{}^{18}O$ enriched water used as a target. The $H_2{}^{18}O$ enriched water containing radioactive fluorine is allowed to pass through, for example, an anion-exchange resin column so that the radioactive fluorine is adsorbed and collected on the column, thereby being separated from the $H_2{}^{18}O$ enriched water. Thereafter, a potassium carbonate solution is allowed to pass through the column to elute the radioactive fluorine, and the eluate is supplemented with a phase transfer catalyst and is evaporated to dryness, thereby activating the radioactive fluorine.

Then, the dried radioactive fluorine is dissolved in acetonitrile, and the syn-1-(N-(t-butoxycarbonyl)amino)-3-[((trifluoromethyl)sulfonyl)oxy]-cyclobutane-1-carboxylic acid ethyl ester, as a precursor, is added to the acetonitrile solution to allow them to react under heating. As a result, radioactive fluorine is added to the precursor, whereby anti-[$^{18}$F]-1-(N-(t-butoxycarbonyl)amino)-3-fluorocyclobutane-1-carboxylic acid ethyl ester is synthesized.

The resultant anti-[$^{18}$F]1-(N-(t-butoxycarbonyl)amino)-3-fluorocyclobutane-1-carboxylic acid ethyl ester is deesterificated and deprotected to yield anti-[$^{18}$F]-FACBC as a target compound. Deesterification and deprotection can be performed, for example, by the method described in the reference (Patent Document; International Publication No. WO97/017092 pamphlet). The amount of the acid to be added need not be restricted as long as the amount can provide an acidic condition sufficient for deprotection.

EXAMPLE

The present invention will be now described in further detail with reference to Examples; however, it should be understood that the details of the Examples are not intended to limit the present invention.

Example 1

Synthesis of syn-1-(N-(t-butoxycarbonyl)amino)-3-[((trifluoromethyl)sulfonyl)oxy]-cyclobutane-1-carboxylic acid ethyl ester Hydrolysis of Syn-Hydantoin (FIG. 1, Step 1)

250 mL of a saturated barium hydroxide solution was added to 6.15 g (corresponding to 25 mmol) of 5-(3-benzyloxycyclobutane)hydantoin and heated under reflux in an oil bath at 114° C. for 24 hours or longer to yield 1-amino-3-benzyloxycyclolbutane-1-carboxylic acid. Then, TLC analysis was performed using, as mobile solvents, two kinds of systems: chloroform/methanol=5/1 (Rf value of syn-hydantoin=around 0.6) and chloroform/methanol=95/1 (Rf value of syn-hydantoin=around 0.3), and the completion of the reaction was confirmed (by coloration with UV and phosphomolybdic acid). Meanwhile, the ratio of syn/anti in hydantoin used in the reaction was about 65/35.

After the completion of the reaction is confirmed, the reaction solution was cooled to room temperature, and about 27 mL of 1 mol/mL sulfuric acid was added to neutralize the reaction solution. After the neutralization, the reaction solution was further stirred at room temperature for 5 minutes, and the formed precipitate was removed by filtration. The filtrate was concentrated to yield 19.07 g of white solid as a mixture of 1-amino-3-benzyloxycyclobutane-1-carboxylic acid and an inorganic salt.

Ethyl Esterification (FIG. 1, Step 2)

19.07 g of 1-amino-3-benzyloxycyclobutane-1-carboxylic acid, which had been fully dried to remove water, was dissolved in 250 mL of ethanol. To this solution, 9.5 mL (corresponding to 75 mmol) of triethylamine was added and cooled at –78° C. for 20 minutes, and then 4.6 mL (corresponding to 62.5 mmol) of thionyl chloride was added. The reaction solution was stirred at 0° C. for 1 hour and at room temperature for 1 hour, followed by heating under reflux in an oil bath at 95° C. overnight. The completion of the reaction was confirmed by TLC analysis using a mobile solvent of chloroform/methanol=95/1 (Rf value of the target compound=around 0.6) (confirmed by coloration with UV and phosphomolybdic acid). After the completion of the reaction is confirmed, the reaction solution was concentrated under reduced pressure to yield 1-amino-3-benzyloxycyclobutane-1-carboxylic acid ethyl ester.

Addition of Boc (FIG. 1, Step 3)

7.64 g of 1-amino-3-benzyloxycyclobutane-1-carboxylic acid ethyl ester was dissolved in 250 mL of a mixed solution of ethanol/triethylamine=9/1. After the solution was cooled in an ice bath for 15 minutes, 8.6 mL (corresponding to 37.5 mmol) of t-butyl dicarbonate was added to the solution and stirred at room temperature overnight. The completion of the reaction was confirmed by TLC analysis using a mobile solvent of hexane/ethyl acetate=1:1 (Rf value of the target reaction product=around 0.6) (confirmed by coloration with UV and molybdic acid). After the completion of the reaction was confirmed, the reaction solution was concentrated under reduced pressure to yield white crystals as a residue. To the residue, 150 mL of cooled ethyl acetate and 150 mL of 0.5 mol/L cooled hydrochloric acid were added, stirred in an ice bath for 5 minutes, and left to stand at room temperature until separation occurred. The organic layer was extracted and washed with 150 mL of water twice, with 150 mL of a saturated aqueous solution of sodium hydrogencarbonate, with 150 mL of water twice and with 150 mL of a saturated saline solution twice in this order, dried with anhydrous sodium sulfate, and concentrated under reduced pressure to yield yellow oily matter. Separately, the water layer was extracted and washed with 150 mL of ethyl acetate twice, with 150 mL of water twice and with 150 mL of saturated saline solution in this order, dried with anhydrous sodium sulfate, and concentrated under reduced pressure to recover a small amount of yellow oily matter. By the series of operations, 8.82 g of light yellow oily matter was obtained. Since it was confirmed with TLC analysis, that there were reagents remaining in the residue, it was briefly purified by silica gel column chromatography (hexane/ethyl acetate=1/1) to yield 4.9282 g (corresponding to 14 mmol) of 1-(N-(t-butoxycarbonyl)amino)-3-benzyloxy-cyclobutane-1-carboxylic acid ethyl ester as white crystals.

Debenzylation (FIG. 1, Step 4)

To 4.9282 g (corresponding to 14 mmol) of 1-(N-(t-butoxycarbonyl)amino)-3-benzyloxy-cyclobutane-1-carboxylic acid ethyl ester, were added 150 mL of ethanol and then 900 mg of palladium-on-activated carbon (10% palladium), and the mixture was purged with hydrogen and stirred at room temperature overnight. After the reaction, palladium-on-activated carbon was removed by filtration using Celite, and the filtrate was concentrated under reduced pressure to yield 5.74 g of white crystals as a residue. The reaction was traced by TLC analysis using a mobile solvent of hexane/ethyl acetate=1/1 (Rf value of the target reaction product=around 0.2) (confirmed by coloration with UV and ninhydrin) to confirm the completion of the reaction. Then, the residue was separated and purified by silica gel column chromatography (hexane/ethyl acetate=1/1, hexane/ethyl acetate=4/1) to yield 1.61 g (corresponding to 6.2 mmol) of 1-(N-(t-butoxycarbonyl)amino)-3-hydroxy-cyclobutane-1-carboxylic acid ethyl ester as white crystals.

Figure 2:
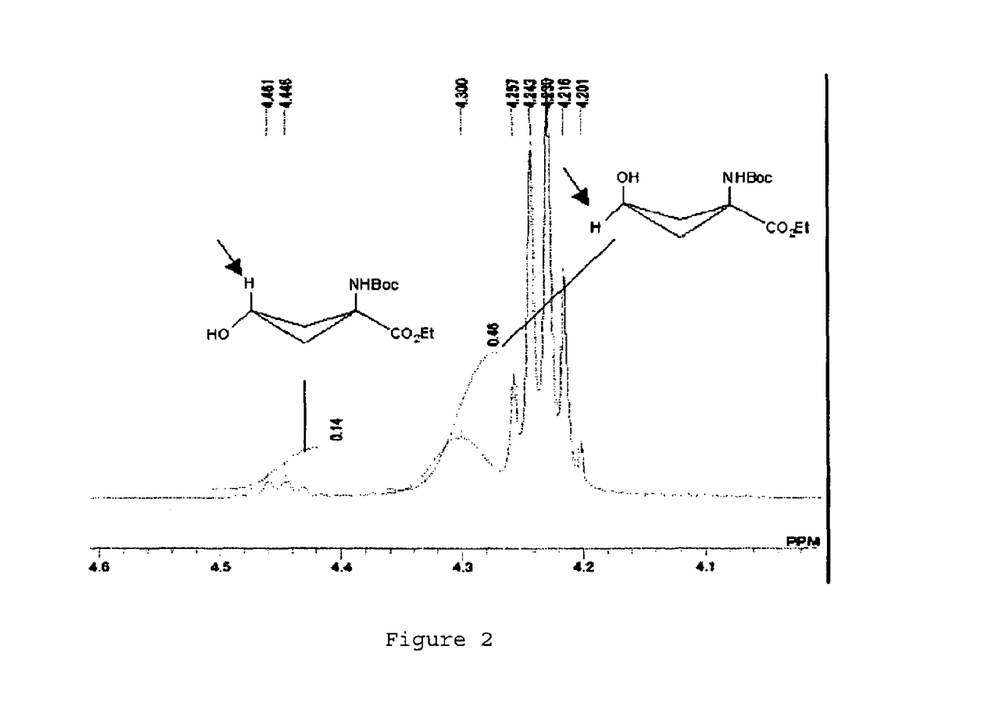
FIG. 2 shows the $^1$H-NMR spectrum of 1-(N-(t-butoxycarbonyl)amino)-3-hydroxy-cyclobutane-1-carboxylic acid ethyl ester.

Based on $^1$H-NMR integrations of the trans-proton bonded to the carbon atom at position 3 of the syn-form and the cis-proton bonded to the carbon atom at position 3 of the anti-form, a molar ratio of the syn-form and the anti-form was estimated to be 14/46 for the obtained 1-(N-(t-butoxycarbonyl)amino)-3-hydroxy-cyclobutane-1-carboxylic acid ethyl ester.

Triflation (FIG. 1, Step 5)

259 mg (1 mmol: the ratio of syn/anti at the initiation of the reaction was 14/46) of 1-(N-(t-butoxycarbonyl)amino)-3-hydroxy-cyclobutane-1-carboxylic acid ethyl ester was dissolved in 4 mL of pyridine and stirred in an ice bath for 20 minutes. Then, 0.26 mL (corresponding to 1.5 mmol) of trifluoromethanesulfonic anhydride was added thereto, and then the mixture was stirred for 30 minutes as it was. The reaction was traced by TLC analysis using a mobile solvent of hexane/diethyl ether=1:1 (Rf value of the target reaction product=around 0.6) (confirmed by coloration with ninhydrin) to confirm the completion of the reaction. TLC showed not only a spot at Rf value=0.4 representing syn-1-(N-(t-butoxycarbonyl)amino)-3-[((trifluoromethyl)sulfonyl)oxy]-cyclobutane-1-carboxylic acid ethyl ester but also a spot at the origin (hexane/diethylether=1/1). After confirming the completion of the reaction, 50 mL of water and 50 mL of ether were added to the reaction solution, and extraction and washing was performed with 50 mL of 1 mol/L hydrochloric acid twice, with 50 mL of water twice and with 50 mL of a saturated saline solution twice in this order. After drying with anhydrous sodium sulfate, concentration under reduced pressure was performed to yield 297.2 mg of light yellow crystals. TLC showed that the spot at the origin disappeared, and thus there were no other spots than the spot at Rf value=0.4 (hexane/diethylether=1/1). The reaction residue was separated and purified by silica gel column chromatography (hexane/diethylether=3:1) to yield 222.8 mg of white crystals which was confirmed by an NMR analysis to be syn-1-(N-(t-butoxycarbonyl)amino)-3-[((trifluoromethyl)sulfonyl)oxy]-cyclobutane-1-carboxylic acid ethyl ester.

The NMR measurement results (internal standard: tetramethylsilane) of the obtained syn-1-(N-(t-butoxycarbonyl)amino)-3-[((trifluoromethyl)sulfonyl)oxy]-cyclobutane-1-carboxylic acid ethyl ester were as follows.

NMR used: JNM-ECP-500 (manufactured by JEOL, Ltd.)
$^1$H-NMR (solvent: CDCl$_3$, resonance frequency: 500 MHz): δ 5.41-5.35 (m, 1H), 5.32 (b, 1H), 4.26 (q, 2H, J=7 Hz), 3.10-3.02 (m, b, 4H), 1.45 (s, 9H), 1.31 (t, 3H, J=7.0 Hz)

INDUSTRIAL APPLICABILITY

The present invention can be used in the field of synthesis of radioactive fluorine-labeled amino acid compounds useful for PET agents, and is useful in the field of radiopharmaceuticals.

The invention claimed is:

1. A process for producing a precursor compound for a radioactive fluorine-labeled organic compound, which comprises:
  a reaction step of allowing a solution containing a mixture of syn- and anti-isomers of a compound represented by the following formula (1):

(1)

wherein, in formula (1), R$_1$ represents a protective group of a carboxyl group, and R$_2$ represents a protective group of an amino group, to react, in a presence of a base, with a compound which reacts with the OH group of the compound represented by the formula (1) to become a leaving group together with the oxygen atom of the OH group, wherein the compound is a straight-chain or branched-chain haloalkylsulfonic acid with 1-9 carbon atoms; and
  a purification step of purifying a reaction solution resulting from the reaction step to obtain a substantially single stereoisomer of a compound represented by the following formula (2):

(2)

wherein, in formula (2), R$_1$ represents a protective group of a carboxyl group, R$_2$ represents a protective group of an amino group, and OR$_3$ represents the leaving group, wherein said purification step is conducted by a liquid-liquid extraction process.

2. The process according to claim 1, wherein the compound which reacts with the OH group of the compound represented by the formula (1) in the reaction step is a straight-chain haloalkylsulfonic acid with 1-9 carbon atoms.

3. The process according to claim 2, wherein the haloalkylsulfonic acid is trifluoromethanesulfonic acid.

4. The process according to claim 3, wherein said trifluoromethanesulfonic acid is in a form of trifluoromethanesulfonic acid anhydride.

5. The process according to claim 1, wherein the base in the reaction step is one or more selected from the group consisting of a straight-chain or branched-chain primary to tertiary alkylamine with 1-10 carbon atoms, a nitrogen-containing heterocyclic compound with 2-20 carbon atoms and a nitrogen-containing hetero aromatic compound with 2-20 carbon atoms.

6. The process according to claim 5, wherein the alkylamine is ethylamine, propylamine, isopropylamine, dimethylamine, diethylamine, dipropylamine, diisopropylamine, trimethylamine, triethylamine or tripropylamine.

7. The process according to claim 5, wherein the nitrogen-containing heterocyclic compound is pyrrolidine, imidazoline, pyrazolidine, piperidine, piperazine, 1,4-diazabicyclo[2.2.2]octane, pyrroline, aziridine or 1,8-diazabicyclo[5.4.0]undeca-7-ene.

8. The process according to claim 5, wherein the nitrogen-containing hetero aromatic compound is pyrrole, pyridine, pyrimidine, pyrazine, triazine, imidazole or pyrazole.

9. The process according to claim 1, wherein the compound which reacts with the OH group of the compound represented by formula (1) in the reaction step is a branched-chain haloalkylsulfonic acid with 1-9 carbon atoms.

* * * * *

UNITED STATES PATENT AND TRADEMARK OFFICE
CERTIFICATE OF CORRECTION

PATENT NO. : 8,563,771 B2
APPLICATION NO. : 12/448311
DATED : October 22, 2013
INVENTOR(S) : Masahito Toyama et al.

It is certified that error appears in the above-identified patent and that said Letters Patent is hereby corrected as shown below:

In the Claims

Claim 1, col. 10, line 15, correct formula (1) to read:

(1)

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,563,771 B2  Page 1 of 1
APPLICATION NO. : 12/448311
DATED : October 22, 2013
INVENTOR(S) : Toyama et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 755 days.

Signed and Sealed this
Fifteenth Day of September, 2015

Michelle K. Lee
*Director of the United States Patent and Trademark Office*